United States Patent
Klauber et al.

(10) Patent No.: US 10,273,216 B2
(45) Date of Patent: Apr. 30, 2019

(54) PROCESS FOR PREPARING CRYSTALLINE METHYL N- [2- [[[1-(4-CHLOROPHENYL)-1H-PYRAZOL-3-YL]OXY]METHYL] PHENYL]-N-METHOXYCARBAMATE

(71) Applicant: BASF SE, Ludwigshafen am Rhein (DE)

(72) Inventors: Eric George Klauber, Bad Duerkheim (DE); Timo Frassetto, Mannheim (DE); Reinhold Niemes, Kindenheim (DE); Ralf Bauer, Worms (DE); Jochen Schroeder, Lambsheim (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 15/751,349

(22) PCT Filed: Aug. 2, 2016

(86) PCT No.: PCT/EP2016/068365
§ 371 (c)(1),
(2) Date: Feb. 8, 2018

(87) PCT Pub. No.: WO2017/025377
PCT Pub. Date: Feb. 16, 2017

(65) Prior Publication Data
US 2018/0230104 A1 Aug. 16, 2018

Related U.S. Application Data

(60) Provisional application No. 62/202,920, filed on Aug. 10, 2015.

(30) Foreign Application Priority Data

Oct. 6, 2015 (EP) .................................... 15188491

(51) Int. Cl.
*C07D 231/22* (2006.01)
*C07D 231/04* (2006.01)
*C07D 231/24* (2006.01)

(52) U.S. Cl.
CPC ......... *C07D 231/22* (2013.01); *C07D 231/04* (2013.01); *C07D 231/24* (2013.01)

(58) Field of Classification Search
CPC .................................................. C07D 231/22
See application file for complete search history.

(56) References Cited

U.S. PATENT DOCUMENTS 6,255,489 B1 7/2001 Klintz
7,816,392 B2 10/2010 Ziegler

FOREIGN PATENT DOCUMENTS

CN 102399190 A 4/2012
CN 104211641 A 12/2014
CN 104592117 A 5/2015

OTHER PUBLICATIONS

Modern Crop Protection Compounds, ed. Kramer, et al., Wiley-VCH Verlag & Co. KGaA, Second Edition, 2012, p. 618.
European Search Report for EP Patent Application No. 15188491.3, dated Feb. 17, 2016, 2 pages.
International Search Report for PCT Patent Application No. PCT/EP2016/068365, dated Sep. 21, 2016, 3 pages.
Lunn, et al., "Validation of Techniques for the Destruction of Dimethyl Sulfate", American Industrial Hygiene Association Journal, vol. 46, Issue 3, 1985, pp. 111-114.
Zheng, et al., "A Review of Synthetic Methods of Pyraclostrobin", Agrochemicals, Issue 6, 2014, pp. 463-465.
International Preliminary Report on Patentability, PCT Patent Application No. PCT/EP20161068365, dated Feb. 13, 2018, 5 pages.

*Primary Examiner* — Shawquia Jackson
(74) *Attorney, Agent, or Firm* — Brinks Gilson & Lione

(57) ABSTRACT

The present invention relates to a process for preparing crystalline methyl N-[2-[[[1-(4-chlorophenyl)-1H-pyrazol-3-yl]oxy]methyl]phenyl]-N-methoxycarbamate (I), comprising
a) reacting a compound of formula II

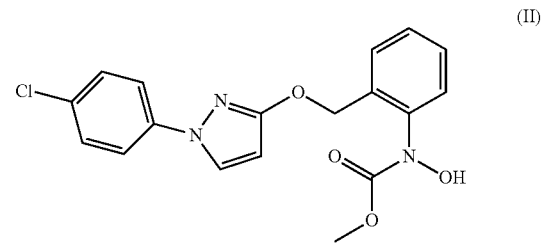

with an alkylating agent in the presence of a base in the presence of a polar solvent selected from alcohols and ketons;
b) the addition of water.

8 Claims, No Drawings

PROCESS FOR PREPARING CRYSTALLINE METHYL N- [2- [[[1-(4-CHLOROPHENYL)-1H-PYRAZOL-3-YL]OXY]METHYL]PHENYL]-N-METHOXYCARBAMATE

This application is a National Stage application of International Application No. PCT/EP2016/068365, filed Aug. 2, 2016, which claims the benefit of U.S. Provisional Application No. 62/202,920, filed Aug. 10, 2015. This application also claims priority under 35 U.S.C. § 119 to European Patent Application No. 15188491.3, filed Oct. 6, 2015.

The present invention relates to a process for preparing crystalline methyl N-[2-[[[1-(4-chlorophenyl)-1H-pyrazol-3-yl]oxy]methyl]phenyl]-N-methoxycarbamate (I), comprising
a) reacting a compound of formula II

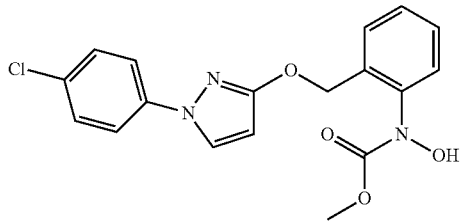

(II)

with an alkylating agent in the presence of a base in the presence of a polar solvent selected from alcohols and ketones;
b) the addition of water.

The production of methyl N-[2-[[[1-(4-chlorophenyl)-1H-pyrazol-3-yl]oxy]methyl]phenyl]-N-methoxycarbamate (I) by reacting a compound of formula II with an alkylating agent is described for example in the review article of Zheng et al (Agrochemicals 2014, 53 (6): 463-465), in Modern Crop Protection Compounds, Vol 2, ©2007 on page 489 or various Chinese patent applications CN104211641A, CN104592117A, CN102399190A and U.S. Pat. No. 6,255,489.

All these documents refer to reaction in solvents, however, the targeted production of crystalline material is not described therein. Crystalline material is advantageous for e.g. producing solvent free water based formulations such as suspension concentrates (SC or FS-formulations).

Usually, the production of crystalline pyraclostrobin requires a further crystallization step, e.g. as described in CN102399190A or U.S. Pat. No. 7,816,392.

Carrying out an alkylation reaction in the presence of alcohols and a base provides certain disadvantages, as unwanted side-reaction of DMS with the alcohol may occur. Am. Ind. Hyg. Assoc. J. 46(3), 111-114 (1985) teaches that 95% of DMS in methanol or ethanol is degraded within 15 min at room temperature in the presence of 1 mol/L aqueous NaOH solution or 1 mol/L $Na_2CO_3$ solution.

Ketones can undergo self-condensation (aldol-reaction) in the presence of bases.

Thus, neither alcohols nor ketones would not be chosen for large scale synthesis processes, usually, polar aprotic solvents would be the preferred option.

Surprisingly, it has been found that the process as described above results in a convenient way to produce crystalline pyraclostrobin at high yields without the necessity to use a further solvent for crystallization as an additional step.

Thus, the present invention relates to a process for preparing crystalline methyl N-[2-[[[1-(4-chlorophenyl)-1H-pyrazol-3-yl]oxy]methyl]phenyl]-N-methoxycarbamate (I), comprising
a) reacting a compound of formula II

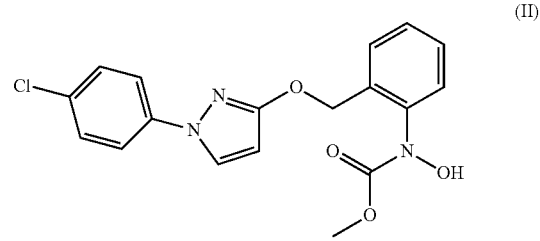 [SMILES: COC(=O)N(O)c1ccccc1COc1ccn(-c2ccc(Cl)cc2)n1]

(II)

with an alkylating agent in the presence of a base in the presence of a polar solvent selected from alcohols and ketones;
b) the addition of water.

The solvent is preferably selected from $C_1$-$C_5$ alcohols or $C_3$-$C_6$ ketones, wherein $C_1$-$C_5$ alcohols are preferred.

Preferred $C_1$-$C_5$ alcohols are methanol, ethanol, n-propanol, isopropanol, n-butanol, isobutanol, 2-butanol and tert-butanol, isoamyalcohol and mixtures thereof, wherein methanol is more preferred Preferred $C_3$-$C_6$ ketones are acetone, methyl-ethyl ketone or butanone (n-butanone, methyl-ethyl-keton), methyl-isobutyl-ketone. More preferred are $C_3$-$C_4$ ketones, such as acetone or butanone.

Suitable bases are generally inorganic compounds and organic bases. Examples for inorganic bases are such as alkali metal and alkaline earth metal hydroxides (eg. lithium hydroxide, sodium hydroxide, potassium hydroxide, magnesium hydroxide and calcium hydroxide), alkali metal and alkaline earth metal oxides (eg. lithium oxide, sodium oxide, calcium oxide and magnesium oxide), alkali metal and alkaline earth metal carbonates (eg. potassium carbonate, sodium carbonate, lithium carbonate, magnesium and calcium carbonate) and also alkali metal hydrogen carbonates (eg. sodium hydrogen carbonate, lithium hydrogen carbonate, potassium hydrogen carbonate, calcium hydrogen carbonate, magnesium hydrogen carbonate) and also alkali metal and alkaline earth metal alkoxides (eg. sodium methoxide, sodium ethoxide, potassium ethoxide, potassium tert-butoxide and dimethoxy-magnesium).

Examples for organic bases are alkali metal and alkaline earth metal alcoholate such as sodium or potassium methanolate, sodium or potassium ethanolate.

Alkali metal and alkaline earth metal hydroxides (eg. lithium hydroxide, sodium hydroxide, potassium hydroxide, magnesium hydroxide and calcium hydroxide), alkali metal and alkaline earth metal carbonates (eg. potassium carbonate, sodium carbonate, (lithium carbonate, magnesium and calcium carbonate) and alkali metal hydrogen carbonates (eg. sodium hydrogen carbonate, lithium hydrogen carbonate, potassium hydrogen carbonate, calcium hydrogen carbonate, magnesium hydrogen carbonate) are particularly preferred.

Suitable methylating agents are methyl chloride, methyl iodide, methyl bromide or methyl sulfonate, methyl sulfate, dimethyl sulfate, methyl brosylate, methyl mesylate, methyl tosylate, methyl triflate, methyl carbonate. Preferred methylating agents are dimethyl sulfate.

The molar ratio of base and compound II can be varied. Usually, the range is from 10:1 to 1:10 for example 5:1 to 1:5, 3:1 to 1:3, 1:1, 1:1.5 and the like.

Analogous ratios apply for the molar ratio of dimethylsulfate:compound II is 10:1 to 1:10 for example 5:1 to 1:5, 3:1 to 1:3, 1:1, 1:1.5 and the like.

The base can be added in solid form or, alternatively dissolved or dispersed in the solvent or in the form of an aqueous solution depending on the solvent and the base chosen.

In the case, the base is present in the form of an aqueous solution, the water content is minimized to an extent that the base is at the limit of solubility of the respective base.

In principle, the water content in the overall solution should be minimized. Preferably, it shall not exceed a concentration of 50% with respect to the solvent, more preferably it shall not exceed 20%.

The amount of water added in step b) shall be sufficient to achieve sufficient precipitation and at least partly solubilize the salts resulting from the reaction, for example the ratio of solvent to added water should not exceed 4:1

In a further embodiment, during the addition of water, seed crystals of pyraclostrobin can be added to facilitate and/or accelerate crystallization.

In general, the reaction temperature in the alkylation is from −78° C. to the boiling point of the reaction mixture, preferably from 0 to 100° C., and particularly preferably from 60 to 90° C.

Due to the presence of salts, the solubility and/or miscibility with water of the respective solvent can be decreased.

Thus, in a further embodiment of the present invention, the process according to the present invention comprises as further step c), which is characterized by the following steps i) to ii):
i) phase separation; and
ii) evaporation of the solvent under reduced pressure or atmospheric pressure.

The invention is further illustrated, but not limited by the following examples:

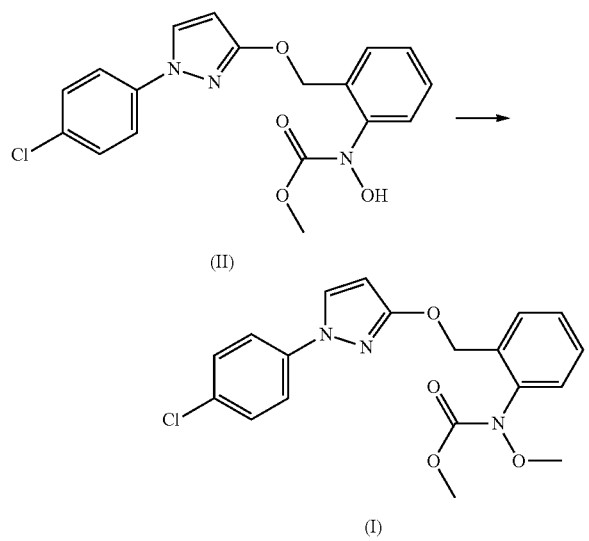

EXAMPLE 1

Reaction and precipitation in methanol: 27.9 g (93.9 wt %, 70 mmol) carbamate (II) were dissolved in 155 g methanol under nitrogen. 26.5 g (210 mmol, 3.0 eq) dimethyl sulfate was added at once followed by 25.1 g of a 47 wt % KOH solution (210 mmol, 3.0 eq) within 5 minutes. The mixture warmed to 49° C. and external heating was applied and the mixture refluxed for 60 min. After cooling to ambient temperature a small amount of seed crystals was added to the mixture and 40 g water were added within 15 min to complete crystallization. The product was filtered and washed with 80 g water. After drying at 50° C. 27.4 g (95.3 wt %, 67 mmol, 96%) product was obtained. The concentrated mother liquor contained no significant amounts of product. 0.9 g product (3% yield) was sticking to the walls of the vessel and was removed by a methanol wash. Total chemical yield: 99%

EXAMPLE 2

Reaction and precipitation in methanol, removal of salts prior to crystallization: 27.9 g (93.9 wt %, 70 mmol) carbamate (II) were dissolved in 155 g methanol under nitrogen. 26.5 g (210 mmol, 3.0 eq) dimethyl sulfate was added at once followed by 25.1 g of a 47 wt % KOH solution (210 mmol, 3.0 eq) within 5 minutes. The mixture warmed to 49° C. and external heating was applied and the mixture refluxed for 60 min. After cooling to ambient temperature inorganic salts were filtered. A small amount of seed crystals was added to the filtrate and 40 g water were added to complete crystallization. The product was filtered and washed with water. After drying at 50° C. 23.1 g (97.4 wt %, 58.0 mmol, 83%) product was obtained. The concentrated mother liquor (8.4 g, 31.8 wt %, 7.1 mmol, 10% yield) contained additional product. 0.23 g product (1% yield) was sticking to the walls of the vessel and was removed by a methanol wash. Total chemical yield: 94%

EXAMPLE 3

Reaction and precipitation in methanol, reduced base/DMS excess: 13.8 g (95.0 wt %, 35.1 mmol) carbamate (II) were dissolved in 77 g methanol under nitrogen. 6.3 g 47 wt % KOH solution (53 mmol, 1.5 eq) were added followed by 6.6 g (52 mmol, 1.5 eq) dimethyl sulfate within 30 minutes. The mixture was heated to 80° C. and post-stirred for 60 min. The mixture was cooled to 50° C., 7.9 g water were added to dissolve the salts and the mixture cooled slowly to 30° C. Another 1.9 g water were added to dissolve precipitated salts. After cooling to 20° C. 90 g water were added slowly to precipitate the product. The product was filtered, washed twice with 20 g water and dried at 40° C. Yield: 13.6 g product (98.3 wt %, 34.5 mmol, 98%).

EXAMPLE 4

Reaction and precipitation in isobutanol 34.2 g (91 mmol) carbamate (II) were dissolved in 205 g isobutanol under nitrogen. 35.0 g (274 mmol, 3.0 eq) dimethyl sulfate were added followed by 32.2 g of a 47 wt % KOH solution (270 mmol, 3.0 eq) within 3 minutes. When the inner temperature had reached 40° C. the mixture was heated to 80° C. and kept for 15 min at this temperature. 207 g water was added at 80° C. and the mixture stirred at this temperature for 1 h to destroy excess dimethyl sulfate. The biphasic mixture was cooled to 40° C. and the phases were separated. The organic phase was washed with 207 g water. The organic phase was concentrated under reduced pressure at 50° C./50 mbar to 220 ml. The mixture was cooled to 12° C., seed crystals added and the mixture kept at 12° C. over night. To complete the precipitation the temperature was lowered to 0° C. The crystalline product was recovered by filtration, washed with water and dried yielding 29.4 g (99.9 wt %, 76 mmol, 83%). Additional product was found in the mother liquor (12%) and on the walls of the reaction vessel (3%) resulting in a total chemical yield of 98%.

EXAMPLE 5

Reaction and precipitation in methyl ethyl ketone:
41.1 g (92.7 wt %, 102 mmol) carbamate (II) were dissolved in 230 g methyl ethyl ketone under nitrogen. 38.6 g (306 mmol, 3.0 eq) dimethyl sulfate was added at once followed by 36.5 g of a 47 wt % KOH solution (306 mmol, 3.0 eq) in one portion. The mixture warmed to 38° C. and external heating was applied and the mixture stirred for 60 min at 80° C. After cooling to ambient temperature 300 g water was added to dissolve the inorganic salts. The phases were separated and the organic phase concentrated until precipitation of the product began. A small amount of seed crystals was added and the mixture stirred for 16 h at room temperature. Filtration and drying at 50° C. produced 32.5 g (93 wt %, 78 mmol, 77%) product. The mother liquor (8.0 g, 61 wt %, 12.6 mmol, 12% yield) contained additional product. 2.5 g product (7% yield) was sticking to the walls of the vessel and was removed by a methanol wash. Total chemical yield: 96%

COMPARISON EXAMPLE 1

Reaction and failed precipitation from toluene:
37.9 g (93.9 wt %, 95 mmol) carbamate (II) were dissolved in 231 g toluene under nitrogen. 36.0 g (286 mmol, 3.0 eq) dimethyl sulfate was added at once followed by 34.1 g of a 47 wt % KOH solution (286 mmol, 3.0 eq) in one portion. The mixture warmed to 35° C. and external heating was applied and the mixture stirred for 15 min at 80° C. 216 g water was added in 40 minutes and the mixture stirred at 80° C. for 1 h. The phases were separated at ambient temperature and the organic phase washed twice with 216 g water. The organic phase was concentrated under reduced pressure at 55° C./50 mbar to a total mass of 87 g. The mixture was cooled to 34° C., 50 mg seed crystals added. As no precipitation occurred the temperature was lowered to 22° C. and another 20 mg seed crystals were added. There was no precipitation, even when the temperature was lowered to 5° C. Eventually the solvent was removed on a rotary evaporator furnishing 38.8 g crude product (91.6 wt %, 92 mmol, 96% yield).

COMPARISON EXAMPLE 2

Reaction and failed precipitation from methyl acetate:
81.9 g (92.7 wt %, 203 mmol) carbamate (II) were dissolved in 526 g methyl acetate under nitrogen. 77.6 g (609 mmol, 3.0 eq) dimethyl sulfate was added at once followed by 72.7 g of a 47 wt % KOH solution (609 mmol, 3.0 eq) in one portion. The mixture warmed to 44° C. and was stirred for 60 min at room temperature. 150 g water was added to dissolve the inorganic salts. The phases were separated and the organic phase concentrated at 300 mbar. Even when the pressure was lowered to 50 mbar to remove methyl acetate completely no precipitation was observed. The product was obtained as a melt.

The invention claimed is:
1. A process for preparing crystalline methyl N-[2-[[[1-(4-chlorophenyl)-1H-pyrazol-3 -yl]oxy]methyl]phenyl]-N-methoxycarbamate (I), comprising
a) reacting a compound of formula II

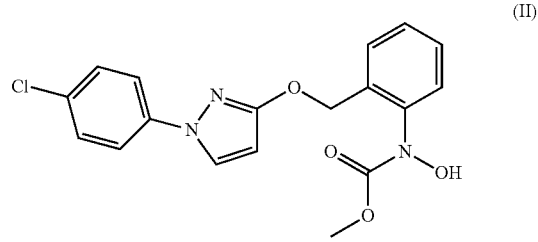 [SMILES: COC(=O)N(O)c1ccccc1COc1ccn(-c2ccc(Cl)cc2)n1]

with an alkylating agent in the presence of a base in the presence of a polar solvent selected from alcohols or ketones followed by
b) addition of water to obtain crystalline methyl N-[2-[[[1-(4-chlorophenyl)-1H-pyrazol-3-yl]oxy]methyl] phenyl]-N-methoxycarbamate (I).
2. The process of claim 1, wherein the solvent is selected from $C_1$-$C_5$ alcohols.
3. The process of claim 1, wherein in the solvent is selected from the group of methanol, ethanol, n-propanol, isopropanol, n-butanol, isobutanol, 2-butanol and tert-butanol, isoamylalcohol and mixtures thereof.
4. The process of claim 1, wherein in the solvent is selected from methanol.
5. The process of claim 1, wherein in the solvent is selected from $C_3$-$C_6$-ketons.
6. The process of claim 5, wherein in the solvent is selected from aceton and methyl ethyl keton.
7. The process of claim 1, wherein in the methylating agent is selected from methyl chloride, methyl iodide, methyl bromide or methyl sulfonate, methyl sulfate, dimethyl sulfate, methyl brosylate, methyl mesylate, methyl tosylate, methyl triflate, methyl carbonate.
8. The process of claim 1, comprising an additional step c) which is characterized by the following steps i) to ii):
  i) phase separation; and
  ii) evaporation of the solvent under reduced or atmospheric pressure.

* * * * *